United States Patent
Kruspe et al.

(10) Patent No.: US 10,337,918 B1
(45) Date of Patent: Jul. 2, 2019

(54) SPECTROMETER WITH FIBER BRAGG GRATING

(71) Applicant: BAKER HUGHES, A GE COMPANY, LLC, Houston, TX (US)

(72) Inventors: Thomas Kruspe, Wietzendorf (DE); Sebastian Jung, Isernhagen (DE)

(73) Assignee: Baker Hughes, A GE Company, LLC, Houston, TX (US)

( * ) Notice: Subject to any disclaimer, the term of this patent is extended or adjusted under 35 U.S.C. 154(b) by 0 days.

(21) Appl. No.: 15/899,445

(22) Filed: Feb. 20, 2018

(51) Int. Cl.
| | |
|---|---|
| *G01D 5/353* | (2006.01) |
| *G01J 3/18* | (2006.01) |
| *G01N 21/25* | (2006.01) |
| *G01L 1/24* | (2006.01) |

(52) U.S. Cl.
CPC ............ *G01J 3/1895* (2013.01); *G01D 5/353* (2013.01); *G01L 1/246* (2013.01); *G01N 21/255* (2013.01)

(58) Field of Classification Search
CPC ....... G01J 3/1895; G01D 5/353; G01L 1/246; E21B 47/00
See application file for complete search history.

(56) References Cited

U.S. PATENT DOCUMENTS

| | | | |
|---|---|---|---|
| 5,615,008 A * | 3/1997 | Stachelek ............ | G01J 3/1804 250/458.1 |
| 6,118,530 A | 9/2000 | Bouevitch et al. | |
| 6,591,024 B2 | 7/2003 | Westbrook | |
| 7,245,369 B2 | 7/2007 | Wang et al. | |
| 7,245,795 B2 | 7/2007 | Walker et al. | |
| 7,327,453 B2 | 2/2008 | Coppeta | |
| 7,411,670 B2 | 8/2008 | Zribi et al. | |
| 7,469,078 B2 * | 12/2008 | Niewczas ............... | G01D 5/268 385/12 |
| 7,817,285 B2 | 10/2010 | Difoggio | |
| 7,852,475 B2 | 12/2010 | Crafts et al. | |
| 7,952,695 B2 | 5/2011 | Crafts et al. | |
| 8,018,597 B2 | 9/2011 | Scott | |

(Continued)

OTHER PUBLICATIONS

Ramuz, Marc, "Transparent, Optical, Pressure-Sensitive Artificial Skin for Large-Area Stretchable Electronics", 2012, Adavance Materials.*

(Continued)

*Primary Examiner* — Maurice C Smith
(74) *Attorney, Agent, or Firm* — Bacewell LLP; Keith R. Derrington (57) ABSTRACT

An optical spectrometer with a tilted or brazed optical grating is useful to identify material composition, estimate physical characteristics, and measure physical conditions. Light from a sample or a space reflects to the grating; and stray light from the grating directed on an optical sensor (which can be a single sensor) and converted into an electrical signal, to obtain information about the sample or space. Examples of scanning include altering an angle the light strays from the optical grating by applying a strain to the optical grating, moving the optical sensor, and installing a mirror in the path of the stray light that reciprocatingly pivots over an angular range. In an example, the optical grating is formed on a light transmission medium that mounts to a piezoelectric element, that expands when energized to apply strain to the grating. In an example, the diffraction grating is a Fiber Bragg Grating.

20 Claims, 5 Drawing Sheets

(56) References Cited

U.S. PATENT DOCUMENTS

| | | | |
|---|---|---|---|
| 8,625,091 B2 | 1/2014 | Villeneuve et al. | |
| 8,699,024 B2 | 4/2014 | Colbourne et al. | |
| 2007/0103682 A1* | 5/2007 | Yoo | G01J 3/02 |
| | | | 356/318 |
| 2009/0074347 A1 | 3/2009 | Xia et al. | |
| 2010/0202726 A1* | 8/2010 | Egalon | G01F 23/2927 |
| | | | 385/12 |
| 2011/0110620 A1* | 5/2011 | Childers | E21B 47/0006 |
| | | | 385/13 |
| 2013/0088710 A1* | 4/2013 | Brastaviceanu | G01B 11/14 |
| | | | 356/72 |
| 2017/0033414 A1* | 2/2017 | Ganguli | H01M 10/48 |

OTHER PUBLICATIONS

Yulong Li, "A plating method for metal coating of fiber Bragg grating", Jun. 13, 2008, Chinese Optics Letters.*
P.S. Westbrook, In-Line Polarimeter Using Blazed Fiber Gratings, IEEE Photonics Technology Letters, vol. 12, No. 10, Oct. 2000.

* cited by examiner

SPECTROMETER WITH FIBER BRAGG GRATING

BACKGROUND OF THE INVENTION

1. Field of Invention

The present disclosure relates in general to a system for use in monitoring conditions in a wellbore. More specifically, the present disclosure relates to a system having a spectrometer that analyzes reflections from an oscillating Fiber Bragg Grating.

2. Description of Prior Art

Spectrometers are used to measure various physical properties of sample substances, as well as their chemical composition. Spectrometers also are used for measuring physical conditions of a space or a sample, such as temperature, strain, pressure, inclination, and acceleration. An optical spectrum analyzer is one type of spectrometer, and which measures optical power as a function of wavelength. Optical spectrum analyzers typically disperse light through a prism or diffraction grating, and employ photosensitive sensors in a path of the dispersed light that detect the light. The photosensitive sensors are usually an array of charge coupled diodes or photodiodes, and which convert the detected light into electrical current.

A Fiber Bragg Grating is one type of diffraction grating used to disperse light to the photosensitive sensors. A Fiber Bragg Grating is a fiber optic member with a central core that has been modified so that its refractive index is altered at discrete distances to define the grating. Typically the alterations follow a periodic pattern that repeats at a designated distance, so that light is reflected at each change of refraction. Generally, the periodic pattern, which is usually referred to as the grating period, is formed to reflect light of a particular wavelength. Most of the light reflected is at a wavelength that is about twice that of the grating period. Thus the wavelength at which most of the light is reflected in the Fiber Bragg Grating is usually identified as the Bragg wavelength. Light at wavelengths outside of the Bragg wavelength passes through the Fiber Bragg Grating and is not reflected. Currently known light sensors for use with optical spectrometers are susceptible to damage when exposed to high temperatures, thereby limiting application of optical spectrometers.

SUMMARY OF THE INVENTION

Disclosed herein is an example of an optical spectrometer which includes a transmission medium having an end in communication with a source of electromagnetic energy, a brazed grating formed in the transmission medium strategically formed so that electromagnetic energy from the source and being transmitted through the transmission medium is directed azimuthally from the transmission medium along the brazed grating to define stray light, and an optical receiver. Included with the optical receiver is a sensor that is responsive to being contacted by the stray light, and an outlet in communication with an analyzer and from which an electrical signal is transmitted that is generated by the stray light contacting the sensor. Also included with this embodiment of the optical spectrometer is a scanning assembly that selectively alters one of, a path of the stray light from the brazed grating, or a position of the optical receiver, so that when the stray light is directed from the transmission medium, the sensor is positioned in a path of the stray light and exposed to at least a portion of the stray light. In an example, the scanning assembly includes an electrically responsive member that when energized experiences a change in size, wherein the electrically responsive member is coupled with the transmission medium and, so that when the electrically responsive member is energized the transmission medium and the grating undergo a change in length that changes a direction of a path of the stray light that is directed from the transmission medium. In one alternative, the electrically responsive member has an amount of piezoelectric material. Optionally, the scanning assembly is a translation system that laterally reciprocates the sensor along a path that is intersected by the stray light. In another alternative, the scanning assembly is a reflective surface that reciprocatingly tilts over a range and is strategically located so that stray light contacting the reflective surface is reflected to the sensor. In one example, the electromagnetic energy is reflected from a sample and wherein a bandwidth of the electromagnetic energy is representative of a chemical composition of the sample. Embodiments exist wherein the electromagnetic energy has light having a discrete bandwidth. Alternatively, the grating is a first grating, and wherein the electromagnetic energy is reflected from a second grating that is disposed within a space, and wherein a bandwidth of the electromagnetic energy is representative of a temperature within the space. Optionally, the sensor and source of electromagnetic energy are disposed in a wellbore. Embodiments exist where the sensor is a single sensor, or two or more photo sensitive elements, such as a photodiode, that are in close proximity to act as a single sensor.

An alternative example of an optical spectrometer is disclosed herein and which includes a brazed optical grating in communication with electromagnetic energy that is within a bandwidth that is representative of information about a sensed subject, the electromagnetic energy refracted from the brazed optical grating in an azimuthal direction from the brazed optical grating, and which defines stray light. This example also includes an optical sensor for receiving the stray light and converting the stray light into electricity and a scanning system for aligning the stray light with the optical sensor.

A method of spectroscopy is also disclosed herein, and which includes receiving electromagnetic energy, refracting the electromagnetic energy from a brazed optical grating to form stray light, and aligning the stray light with an optical sensor, so that an output of the optical sensor represents spectral information about the electromagnetic energy. In one embodiment, a spectrum of the electromagnetic energy contains compositional information about a sample. Optionally, a spectrum of the electromagnetic energy contains information about a temperature of a space. The step of aligning alternatively includes applying an axial force to the brazed optical grating by energizing a piezoelectric member with an amount of electricity so that the stray light is directed to the optical sensor. In an example, a voltage of the electricity correlates to a temperature of a space sensed with the electromagnetic energy. In one embodiment, the step of aligning includes reciprocating the optical sensor along a path that is oblique with a transmission medium that carries the electromagnetic energy, and substantially orthogonal with a path of the stray light. Optionally, the step of aligning involves tilting a reflective surface in a path of the stray light so that the stray light is scanned across the optical sensor. In one alternative, the optical sensor and a source of the electromagnetic energy are disposed in a wellbore. Embodiments exist where the optical sensor is a single optical sensor, or two or more photo sensitive elements, such as a photodiode, that when combined act as a single optical sensor.

BRIEF DESCRIPTION OF DRAWINGS

Some of the features and benefits of the present invention having been stated, others will become apparent as the description proceeds when taken in conjunction with the accompanying drawings, in which.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The method and system of the present disclosure will now be described more fully hereinafter with reference to the accompanying drawings in which embodiments are shown. The method and system of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout. In an embodiment, usage of the term "about" includes +/−5% of the cited magnitude. In an embodiment, usage of the term "substantially" includes +/−5% of the cited magnitude.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Figure 1:
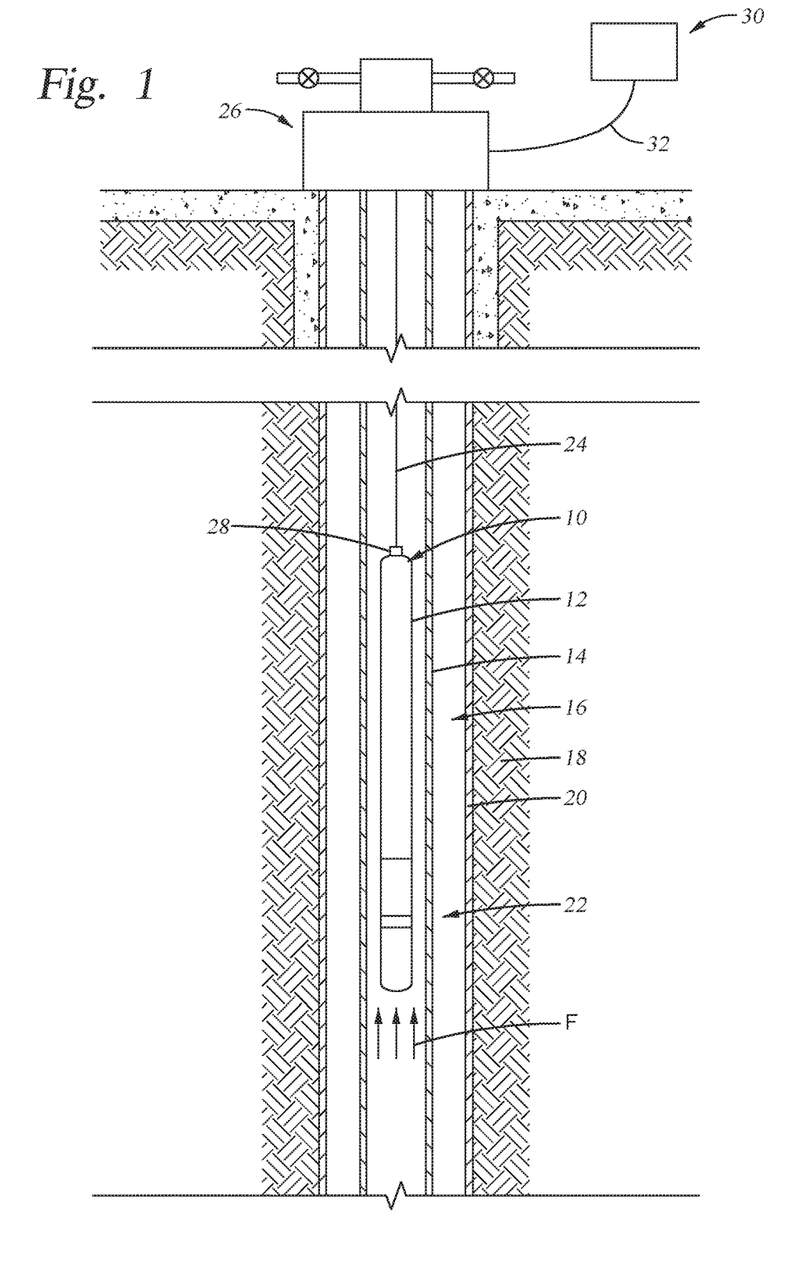
FIG. 1 is a side partial sectional view of a downhole tool in a wellbore and which includes an example of an optical spectrometer.

FIG. 1 shows in a side partial sectional view an example of a downhole tool 10 which includes an elongated housing 12 having a substantially curved outer circumference. The tool 10 is coaxially disposed within a string of tubing 14 and which is set in a wellbore 16 that intersects a subterranean formation 18. Wellbore 16 is lined with casing 20, and which circumscribes tubing 14. Other embodiments exist where tool 10 is disposed within an open hole wellbore that is not lined with casing, or a wellbore without tubing. Within housing is a downhole analyzer 22, which as will be described in more detail below, is useful for analyzing conditions and properties downhole. For example, sensor 22 is useful for obtaining temperatures within wellbore 12, and in other embodiments analyzes the chemical compounds or constituents of solids or fluids sampled within wellbore 16. Tool 10 is suspended in the wellbore 16 on a conveyance means 24, which provides a means for deploying tool 10 in wellbore 16, and also provides a medium for data and control signals between surface and tool 10. Examples of the conveyance means 24 include wireline, slick line, cable, coiled tubing, and any other currently known or later developed means for deploying and controlling tools downhole. In an alternative example, tool 10 is included as part of a logging/measuring while drilling operation. Capping the wellbore 16 is a wellhead assembly 26 which provides pressure control and selective ingress to wellbore 16. An optional cablehead connector 28 is shown mounted on an upper end of housing 12, and provides a connection point for conveyance means 24 to tool 10. An optional controller 30 is schematically illustrated on surface and outside of the wellbore 16, and which includes a memory and communications means for controlling and/or communicating with tool 10 and via communication means 32. Example of communication means 32 include hardwire, fiber optics, and wireless signals.

Figure 2:
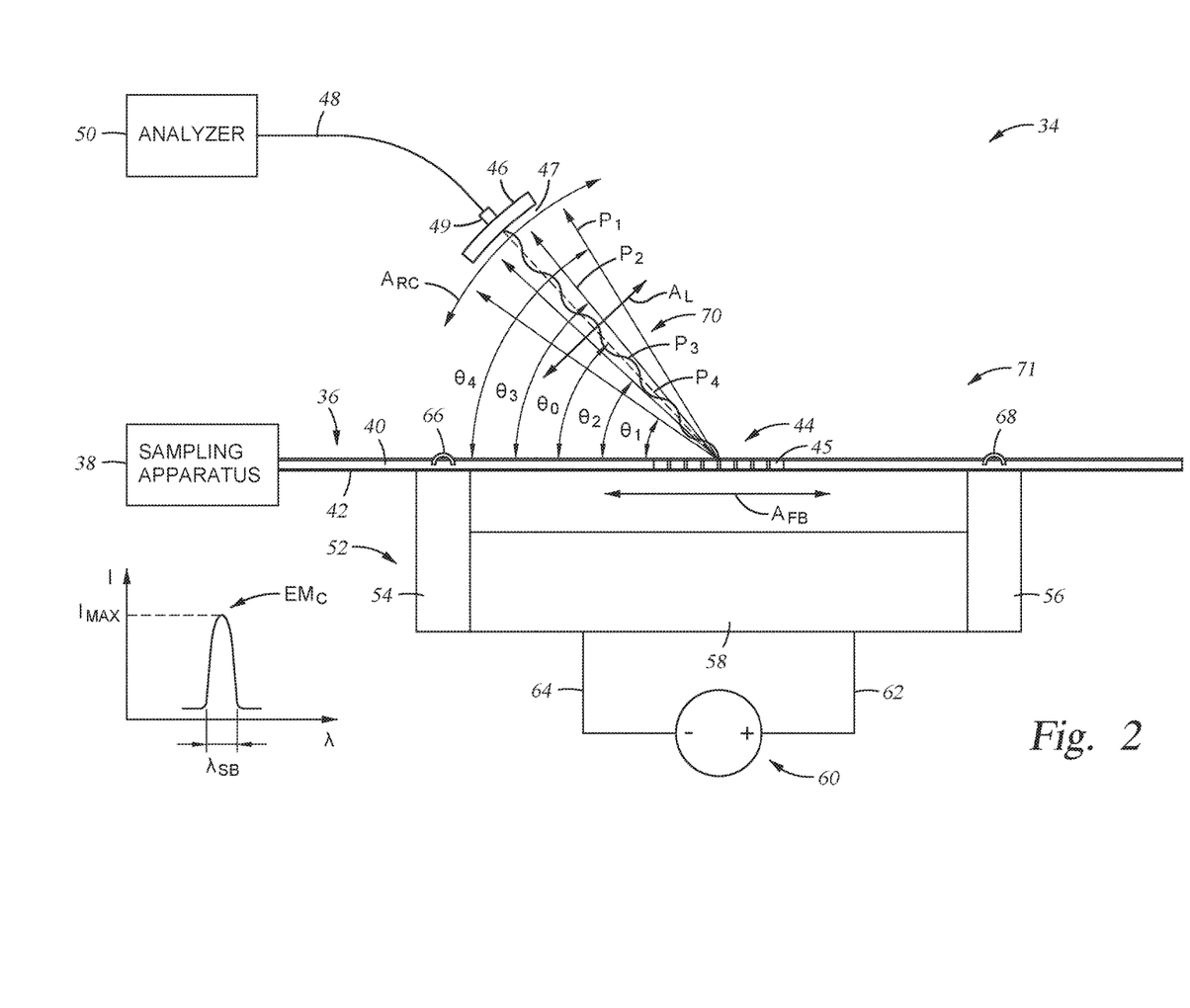
FIG. 2 is a schematic example of an optical spectrometer for use with the downhole tool of FIG. 1.

An example of a spectrometer 34 is schematically illustrated in a side partial sectional view in FIG. 2. Example applications for spectrometer 34 include estimating temperature(s) in the wellbore 16 (FIG. 1), identifying substances downhole, and identifying chemical compositions of substances downhole. In an embodiment, the substances are collected by tool 10 while in the wellbore 16, and the analysis with the spectrometer 34 is conducted while the tool 10 remains in the wellbore 16. Included with this embodiment of this spectrometer 34 is a transmission medium 36 shown having an end in communication with a sampling apparatus 38. In one example, transmission medium 36 includes a fiber optic core 40 which is a substantially transparent member and provides a medium for the transmission of electromagnetic energy, such as light. Electromagnetic energy is transmitted from sampling apparatus 38 to spectrometer 34 via transmission medium 36. Electromagnetic energy is received within sampling apparatus 38 and then directed into a space or onto a substance. When interrogating the space or substance, one or more properties of the electromagnetic energy are altered to define conditioned electromagnetic energy $EM_C$. In the example of FIG. 2, the conditioned electromagnetic energy $EM_C$ is a signal of light having a bandwidth $\lambda_{SB}$, the maximum intensity $I_{MAX}$ of the signal occurs at a wavelength within bandwidth $\lambda_{SB}$. Analyzing the conditioned electromagnetic energy $EM_C$, such as with the spectrometer 34, yields information about the space (i.e. a temperature in the space) or sampled substance. Information about the sampled substance include identification of the substance itself, as well as identification of constituents within the sub stance.

A cladding 42 circumscribes core 40 and provides protection as well as a surface from which the electromagnetic energy internally reflects as it is being transmitted along the transmission medium 36. In the example of FIG. 2, included within core 40 is a Fiber Bragg Grating 44. In this example, the Fiber Bragg Grating 44 is brazed or tilted, and formed from a number of gratings 45 that represent a change in an index of refraction within the core 40. Spaced obliquely from the Fiber Bragg Grating 44 is a receiver 46 and which includes a sensor 47 on a side facing the Fiber Bragg Grating 44. In one non-limiting example, the receiver 46 is a photodiode which receives electromagnetic energy in the form of light and converts the light into electricity, and sensor 47 represents the semi-conductor material within photodiode where the conversion occurs. Receiver 46 is coupled to and in communication with another transmission medium 48. An outlet 49 is mounted on an end of receiver 46 opposite from sensor 47, and which provides connection between receiver and transmission medium 48. An end of transmission medium 48 distal from receiver 46 connects to an analyzer 50 and which contains hardware and software for analyzing signals from receiver 46 transmitted through transmission medium 48.

Still referring to the example of FIG. 2, transmission medium 36 mounts to and is supported on a support member 52 which is shown having a pair of spaced-apart frame elements 54, 56. Frame elements 54, 56 contact portions of transmission medium 36 on opposing sides of Fiber Bragg Grating 44. Spanning between the frame elements 54, 56 is a piezoelectric member 58 which when energized experiences a change in length. Piezoelectric member 58 is selectively energized by a power source 60 is shown having leads 62, 64 connected thereto and where ends of leads 62, 64 distal from power source 60 are in electrical contact with the piezoelectric member 58. Attachment points 66, 68 are illustrated where the transmission medium 36 is supported on the frame elements 54, 56 and which attach the transmission medium 36 to the frame elements 54, 56 at these locations. The tilted or brazed gratings 45 of Fiber Bragg Grating 44 introduce a refractive change into the transmission medium 36 that diffract electromagnetic energy within a particular bandwidth, and azimuthally from the transmission medium 36. In one example and for the purposes of discussion herein, the phrase "azimuthally from the transmission medium 36" means that the diffracted light is directed along one or more optical paths having differing projections onto a plane oriented normal to an axis of grating 45. In the example of FIG. 2, the conditioned electromagnetic magnetic energy $EM_C$ diffracted by Fiber Bragg Grating 44 is stray light 70, which diffracts from the Fiber Bragg Grating 44 at an angle $\theta_0$ that is oblique to core 40, and where angle $\theta_0$ is dependent on a wavelength of the conditioned electromagnetic magnetic energy $EM_C$. Path $P_0$ illustrates an example route of stray light 70 leaving Fiber Bragg Grating 44.

As shown by double-headed arrow $A_{FB}$ (which runs substantially parallel with transmission medium 36) by energizing piezoelectric member 58 with electricity from power source 60 via leads 62, 64, piezoelectric member 58 is elongated. Elongating piezoelectric member 58 urges frame elements 54, 56 away from one another. As the transmission medium 36 is attached to frame elements 54, 56 at attachment points 66, 68, moving the frame elements 54, 56 further away from one another stretches a portion of transmission medium 36 between attachment points 66, 68 and produces an internal strain within this portion of transmission medium 36. Straining transmission medium 36 as shown consequently applies a corresponding strain to Fiber Bragg Grating 44 thereby altering a path of the light 70 that is refracted from the gratings within the Fiber Bragg Grating 44. As shown, applying the strain to the transmission medium 36 and Fiber Bragg Grating 44, the stray light 70 refracted from the Fiber Bragg Grating 44 is selectively directed along a series of different paths $P_{1-4}$, which are illustrated as being oriented at oblique angles $\theta_{1-4}$ from core 40. Directing the stray light 70 along the different paths $P_{1-4}$ scans the stray light 70 along an arcuate length $A_{RC}$ to ensure the receiver 46 is illuminated with an amount of stray light 70 so that a signal or series of signals are generated by sensor 47, and directed into transmission medium 48 for analysis by analyzer 50. The scanning technique described herein is employed to align the receiver 46 with the stray light 70 so that the amount of stray light 70 illuminating the sensor 67 is sufficient to extract information from the conditioned electromagnetic energy $EM_C$ received from sampling apparatus 38.

Further in the example of FIG. 2, the combination of the piezoelectric member 58, power source 60, leads 62, 64, and frame elements 54, 56 define an example of a scanning assembly 71. As noted above, an advantage of the scanning assembly 71 is that the receiver 46 with its sensor 47 is irradiated with a sufficient amount of stray light 70 so that meaningful analysis results are obtained. Employing the example scanning assembly 71 provides a significant advantage over the currently known use of arrays of sensing devices, which are not capable of operating in high temperature situations, such as those often experienced within a wellbore. In an embodiment, high temperature situations are those where temperature is at least about 250° F. for a period of time exceeding 1 hour. Another advantage of the method and system described herein is that the stray light 70 is directed to a precise location so that embodiments exist where the receiver 46 is a single receiver and/or the sensor 47 is a single sensor. Further alternatives exist where receiver 46 or sensor 47 include two or more receivers 46 or sensors 47 disposed proximate one another and that act as a single receiver 46 or sensor 47.

Figure 3:
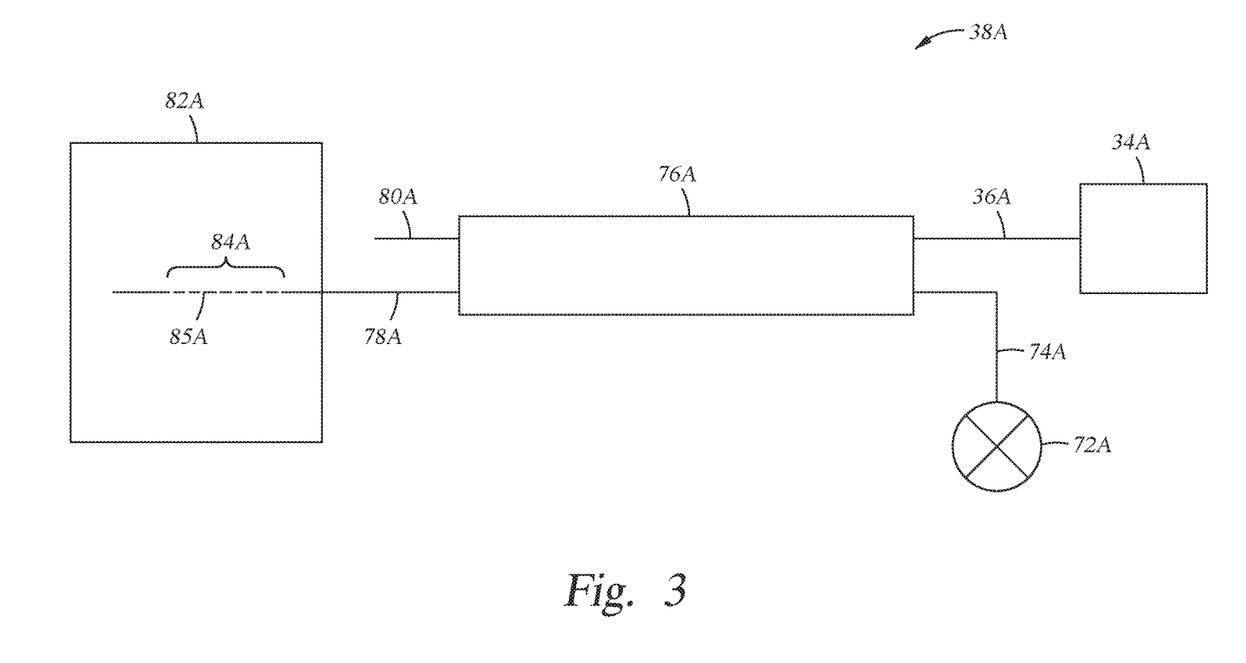
FIG. 3 is a schematic example of an embodiment of a temperature sensor for use with the optical spectrometer of FIG. 2.

FIG. 3 is a schematic example of one embodiment of a sampling apparatus 38A and shown having a source 72A of electromagnetic energy. In an example, source 72A generates light, and is optionally a superluminescent light emitting diode. An example of a transmission medium 74A is depicted having an end coupled to source 72A, which transmits electromagnetic energy generated by source 72A to a splitter 76A. On an end of splitter 76A distal from transmission medium 74A, a pair of additional transmission mediums 78A, 80A are shown extending from splitter 76A on an end opposite from transmission medium 74A. An end of transmission medium 78A distal from splitter 76A projects into a space 82A where temperature is being sensed with the sampling apparatus 38A. In an example, space 82A is within wellbore 16 (FIG. 1), and which alternatively is within or outside of tool 10. A diffraction grating 84A is formed within the transmission medium 78A and in a portion within space 82A, where in one embodiment diffraction grating 84A is a Fiber Bragg Grating. Gratings 85A in the transmission medium 78A define changes in the refractive index of the transmission medium 78A.

In a non-limiting example of operation of the sampling apparatus 38A, electromagnetic energy from source 72A travels to diffraction grating 84A via transmission mediums 74A, 78A and splitter 76A. In the illustrated example, gratings 85A have a grating period, so that electromagnetic energy from source 72A having a designated wavelength, or range of wavelengths, is reflected from diffraction grating 84A back towards splitter 76A. The portion of electromagnetic energy in transmission medium 78A that is outside of the designated wavelength or range of wavelengths is transmitted past diffraction grating 84A. Moreover, the wavelength or range of wavelengths reflected by diffraction grating 84A is dependent on the temperature in the space 82A. In this example, the electromagnetic energy reflected from diffraction grating 84A, and thus reflected from gratings 85A, is that within bandwidth 43. The reflected electromagnetic energy is directed back through transmission 78A, into splitter 76A and exits into transmission medium 36A, where it is then guided to the spectrometer 34A.

Further in the example of FIG. 3, a particular voltage is applied to the piezoelectric material 58 (FIG. 2), which in turn strains the Fiber Bragg Grating 44 a designated amount, so that the stray light 70 exiting the transmission medium 36 is directed along a designated path. For the purposes of discussion herein, a designated path of the stray light 70 (such as one of paths $P_{1-4}$), is one that irradiates receiver 46 with stray light 70, and with sufficient illumination, so that receiver 46 generates electrical signals that yield an estimate of temperature in space 82A when analyzed with analyzer 50. As indicated above, the angle at which the electromagnetic energy reflects from the Fiber Bragg Grating 44 depends at least in part on the wavelength of the stray light 70. Also, because the wavelength of the stray light 70 is the same as the electromagnetic energy that reflects from the diffraction grating 84A, changes in temperature of the space 82A (FIG. 3) alter the wavelength of electromagnetic energy directed to Fiber Bragg Grating 44 via transmission medium 36. Changes in temperature in the space 82A therefore necessarily alter the angle from which the stray light 70 exits the Fiber Bragg Grating 44. Thus, by observing the voltage being applied to the piezoelectric material 58 when the stray light 70 is reflected along a one of the paths $P_{1-4}$ that sufficiently illuminate receiver 46 to obtain meaningful results, the voltage can be correlated to the temperature within the space 82A. This correlation can be done theoretically or empirically.

Figure 4:
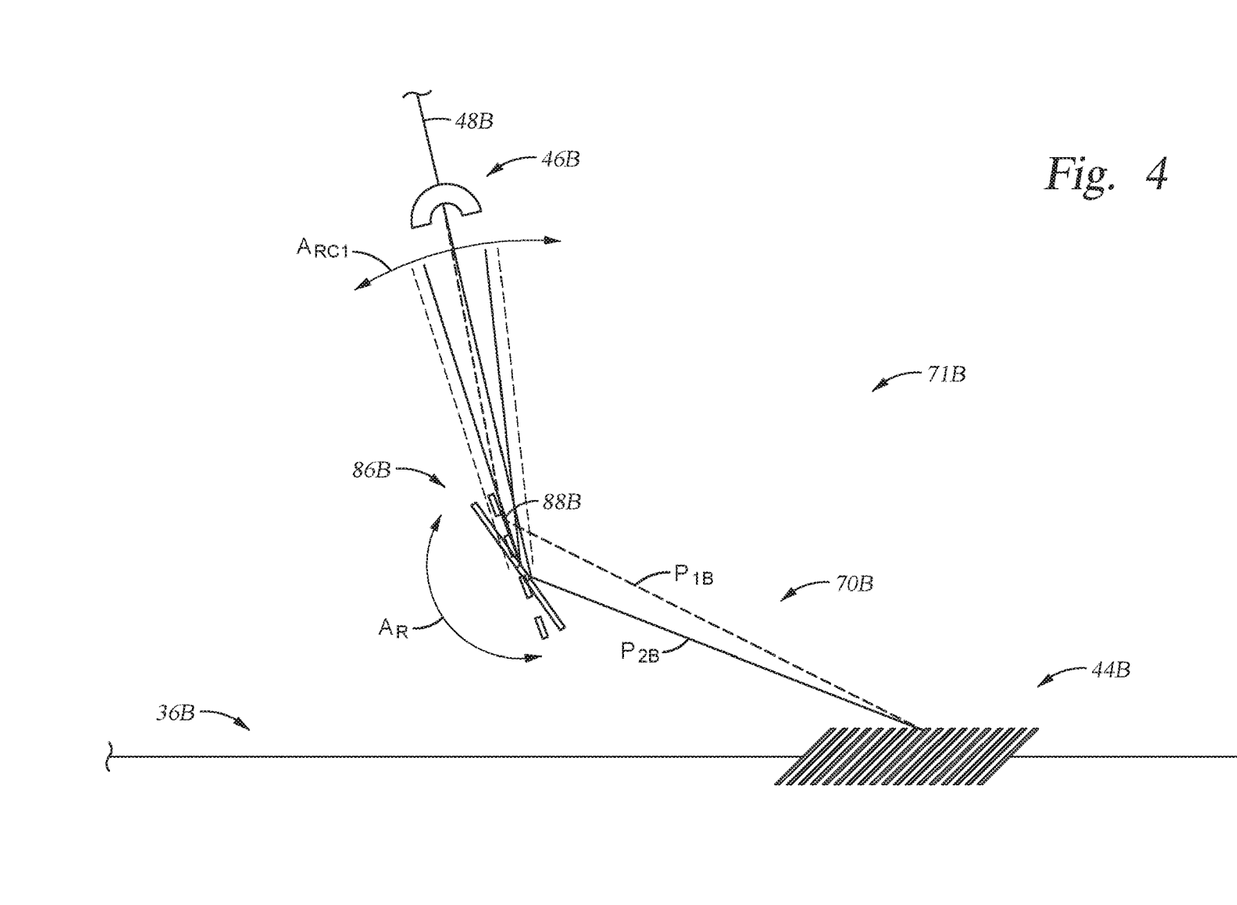
FIG. 4 is a schematic example of an alternate embodiment of a portion of the optical spectrometer of FIG. 2.

Another example of a scanning assembly 71B is represented in schematic form in FIG. 4. Here, stray light 70B refracted from Fiber Bragg Grating 44B is shown projecting along a pair of non-parallel paths $P_{1B}$, $P_{2B}$, and where both paths $P_{1B}$, $P_{2B}$ are redirected so that stray light 70B traveling along either of paths $P_{1B}$, $P_{2B}$ illuminate receiver 46B. Construction of the Fiber Bragg Grating 44B dictates the direction of the path of the stray light 70B refracted from Fiber Bragg Grating 44B, and is based on the wavelength of the electromagnetic energy in the transmission medium 36B. A pivoting reflector 86B is shown strategically located and sized to accommodate for the range in angles over which stray light 70B leaves the Fiber Bragg Grating 44B. The reflector 86B in set the potential pathways of stray light 70B, and includes a reflective surface 88B facing in the direction of the Fiber Bragg Grating 44B. A rotation means (not shown) pivots reflector 86B about an axis that is transverse to the paths $P_{1B}$, $P_{2B}$ so that the stray light 70B reflected from reflective surface 88B is scanned across receiver 46B along an arcuate range $A_{RC1}$ so that a sufficient amount the stray light 70B irradiates receiver 46B to obtain wavelength and intensity information about the stray light 70B. In the example of FIG. 4, the relative locations of the Fiber Bragg Grating 44B and receiver 46B remain substantially constant, and characteristics of the Fiber Bragg Grating 44B remain substantially constant as well.

Figure 5:
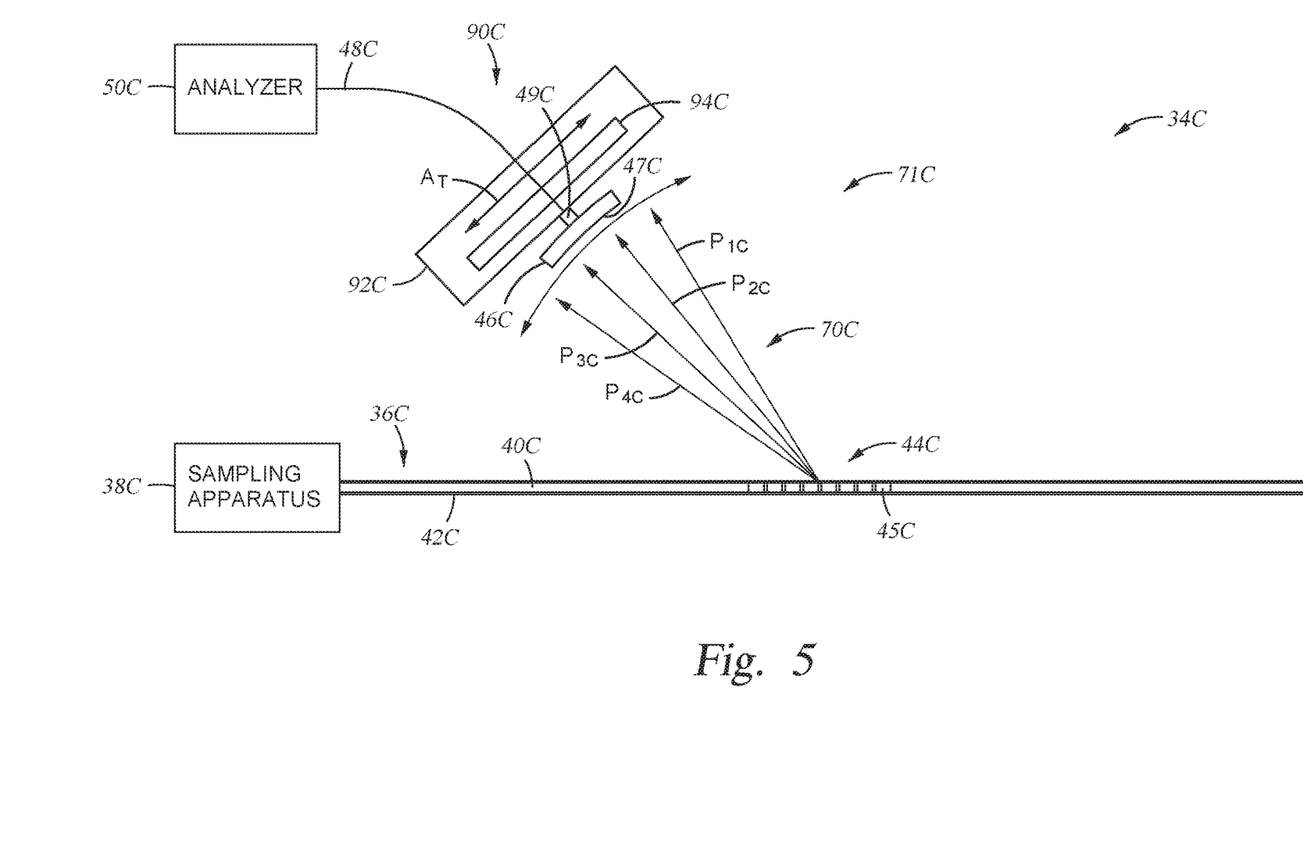
FIG. 5 is a schematic example of an alternate embodiment of the optical spectrometer of FIG. 2.

Shown in schematic form in FIG. 5 is another example of a spectrometer 34C and having a scanning assembly 71C so that a receiver 46C and sensor 47C is illuminated with a sufficient amount of stray light 70B being refracted from Fiber Bragg Grating 44C so that intensity and wavelength information about the stray light 70B is obtained from an output of the receiver 46C and sensor 47C. Here, the electromagnetic energy within transmission medium 36C is provided from a sampling apparatus 38C and transmitted within core 40C. On contacting the gratings 45C within Fiber Bragg Grating 44C, the light 70C is refracted on a number of different paths $P_{1C-4C}$, depending on a wave length of the electromagnetic energy being refracted from gratings 45C. In an embodiment, the scanning assembly 71C translates the receiver 46C laterally and along a path illustrated by arrow $A_T$ which is generally orthogonal to the paths $P_{1C-4C}$. In an example, scanning assembly 71C moves receiver 46C and sensor 47C reciprocatingly towards and away from paths $P_{1C-4C}$, and on lateral sides of each of the paths $P_{1C-4C}$. In the illustrated embodiment, the receiver 46C and sensor 47C mounts to an example of a translation system 90C that reciprocates the receiver 46C in the motion as shown and described above. Included with translation system 90C is a base 92C on which a reciprocating harness 94C is mounted. The receiver 46C couples to the harness 94C, so that receiver 46C moves with movement of the harness 94C, and thereby provides a scanning function so that the receiver 46C and sensor 47C are illuminated with a sufficient amount of stray light 70C to obtain information about the electromagnetic energy being received from sampling apparatus 38C.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. For example, the device can be permanently or temporarily disposed downhole. In other embodiments, the device and method disclosed herein is used to measure one or more of acceleration, magnetic field, inclination, velocity, displacement, force or other physical or chemical properties. In the example of measuring acceleration, a proof mass (m) is used to convert acceleration (a) into force (F): F=(m)(a); where the force is measured by the strain reacting on Fiber Bragg Grating. In an example of measuring inclination, a proof mass (m) is used to convert gravity (g) into force (F): F=(m)(g), in one example the force reacting on six optical fibers is measured by three or six Fiber Bragg Gratings to deduce the gravity direction, which indicates inclination. In an alternative, magnetic field is measured by observing a strain in a magnetostrictive material resulting from an applied magnetic field, which is transferred to an optical fiber and measured by a Fiber Bragg Grating. Displacement, in one example, is measured by transferred a displacement to strain in an optical fiber and measured by a Fiber Bragg Grating. In an example of measuring force, the force is transferred to strain in an optical fiber and measured by a Fiber Bragg Grating. These and other similar modifications will readily suggest themselves to those skilled in the art, and are intended to be encompassed within the spirit of the present invention disclosed herein and the scope of the appended claims.

What is claimed is:

1. An optical spectrometer comprising:
   a transmission medium having an end in communication with a source of electromagnetic energy;
   a grating formed in the transmission medium strategically formed so that electromagnetic energy from the source and being transmitted through the transmission medium is directed azimuthally from the transmission medium along the grating to define stray light;
   an optical receiver having,
     a sensor that is responsive to being contacted by the stray light and, and
     an outlet in communication with an analyzer and from which an electrical signal is transmitted that is generated by the stray light contacting the sensor; and
   a scanning assembly that selectively alters one of, a path of the stray light from the grating, or a position of the optical receiver, so that when the stray light is directed from the transmission medium, the sensor is positioned in a path of the stray light and exposed to at least a portion of the stray light, the scanning assembly comprising an electrically responsive member that when energized experiences a change in size or shape.

2. The optical spectrometer of claim 1, wherein the electrically responsive member is coupled with the transmission medium and, so that when the electrically responsive member is energized the transmission medium and the grating undergo a change in length that changes a direction of a path of the stray light that is directed from the transmission medium.

3. The optical spectrometer of claim 2, wherein the electrically responsive member comprises an amount of piezoelectric material.

4. The optical spectrometer of claim 1, wherein the sensor comprises a photodiode.

5. The optical spectrometer of claim 1, wherein the scanning assembly comprises a translation system that laterally reciprocates the sensor along a path that is intersected by the stray light.

6. The optical spectrometer of claim 1, wherein the scanning assembly comprises a reflective surface that reciprocatingly tilts over a range and is strategically located so that stray light contacting the reflective surface is reflected to the sensor.

7. The optical spectrometer of claim 1, wherein the electromagnetic energy is reflected from a sample and wherein a bandwidth of the electromagnetic energy is representative of a chemical composition of the sample.

8. The optical spectrometer of claim 1, wherein the electromagnetic energy comprises light having a discrete bandwidth.

9. The optical spectrometer of claim 1, wherein the grating comprises a first grating, and wherein the electromagnetic energy is reflected from a second grating that is disposed within a space, and wherein a bandwidth of the electromagnetic energy is representative of a temperature within the space.

10. The optical spectrometer of claim 1, wherein the sensor and source of electromagnetic energy are disposed in a wellbore.

11. An optical spectrometer comprising:
a brazed optical grating in communication with electromagnetic energy that is within a bandwidth that is representative of information about a sensed subject, the electromagnetic energy refracted from the brazed optical grating in an azimuthal direction from the brazed optical grating, and which defines stray light;
a single optical sensor for receiving the stray light and converting the stray light into electricity; and
a scanning system comprising an electrically responsive member that when energized experiences a change in size or shape for aligning the stray light with the single optical sensor.

12. A method of spectroscopy comprising:
receiving electromagnetic energy;
refracting the electromagnetic energy from a brazed optical grating to form stray light;
obtaining a scanning assembly having an electrically responsive member that when energized changes size or shape, and that is coupled with the brazed optical grating; and
deforming the brazed optical grating to align the stray light with an optical sensor by energizing the electrically responsive member, so that an output of the optical sensor represents spectral information about the electromagnetic energy.

13. The method of claim 12, wherein a spectrum of the electromagnetic energy comprises compositional information about a sample.

14. The method of claim 12, wherein a spectrum of the electromagnetic energy comprises information about a temperature of a space.

15. The method of claim 12, wherein the step of deforming comprises applying an axial force to the brazed optical grating by energizing a piezoelectric member with an amount of electricity so that the stray light is directed to the optical sensor.

16. The method of claim 15, wherein a voltage of the electricity correlates to a temperature of a space sensed with the electromagnetic energy.

17. The method of claim 12, wherein the step of aligning comprises reciprocating the optical sensor along a path that is oblique with a transmission medium that carries the electromagnetic energy, and substantially orthogonal with a path of the stray light.

18. The method of claim 12, wherein the step of aligning comprises tilting a reflective surface in a path of the stray light so that the stray light is scanned across the optical sensor.

19. The method of claim 12, wherein the optical sensor and a source of the electromagnetic energy are disposed in a wellbore.

20. The method of claim 12, wherein the optical sensor comprises a single optical sensor.

* * * * *